United States Patent [19]

Celmer et al.

[11] 4,148,882

[45] Apr. 10, 1979

[54] POLYCYCLIC ETHER ANTIBIOTICS PRODUCED BY NEW SPECIES OF ACTINOMYCETE

[75] Inventors: Walter D. Celmer, New London; Walter P. Cullen, East Lyme; Charles E. Moppett, Mystic; John R. Oscarson, Pawcatuck; Liang H. Huang, East Lyme, all of Conn.; Riichiro Shibakawa, Handa; Junsuke Tone, Chita, both of Japan

[73] Assignee: Pfizer Inc., New York, N.Y.

[21] Appl. No.: 809,620

[22] Filed: Jun. 24, 1977

[51] Int. Cl.$^2$ ............................................. A61K 35/00

[52] U.S. Cl. .................................... 424/122; 424/115; 195/80 R

[58] Field of Search .............. 195/80 R; 424/115, 122

[56] References Cited

U.S. PATENT DOCUMENTS 3,985,872  10/1976  Chamberlin ......................... 424/122

*Primary Examiner*—Jerome D. Goldberg
*Attorney, Agent, or Firm*—Connolly and Hutz

[57] ABSTRACT

New polycyclic ether antibiotics produced by a species of actinomycete under submerged fermentation conditions are useful in controlling coccidiosis in poultry and in improving feed utilization efficiency in ruminants.

9 Claims, 5 Drawing Figures

Infrared Absorption Spectrum of Free Acid of Compound A7,433

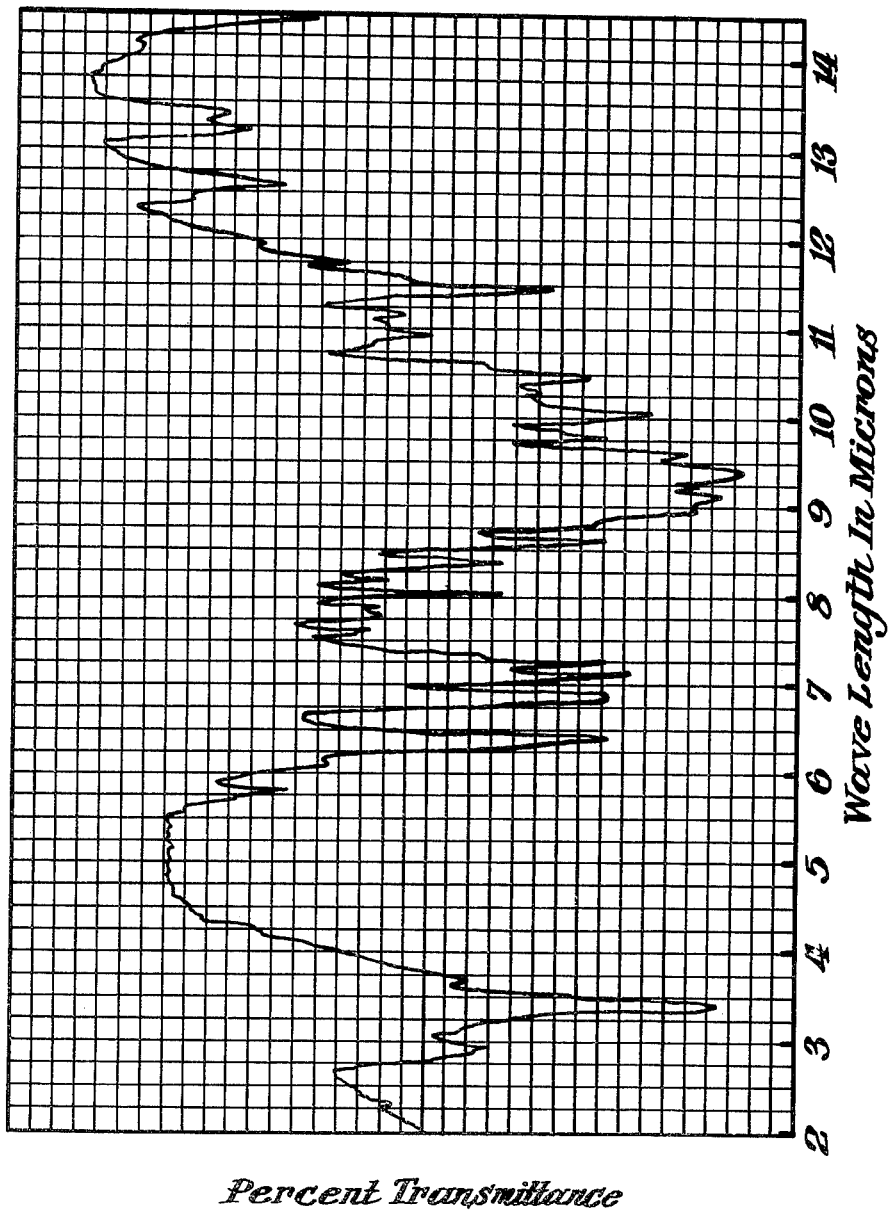
Fig. 2. Infrared Absorption Spectrum of Sodium Salt of Compound 47,483

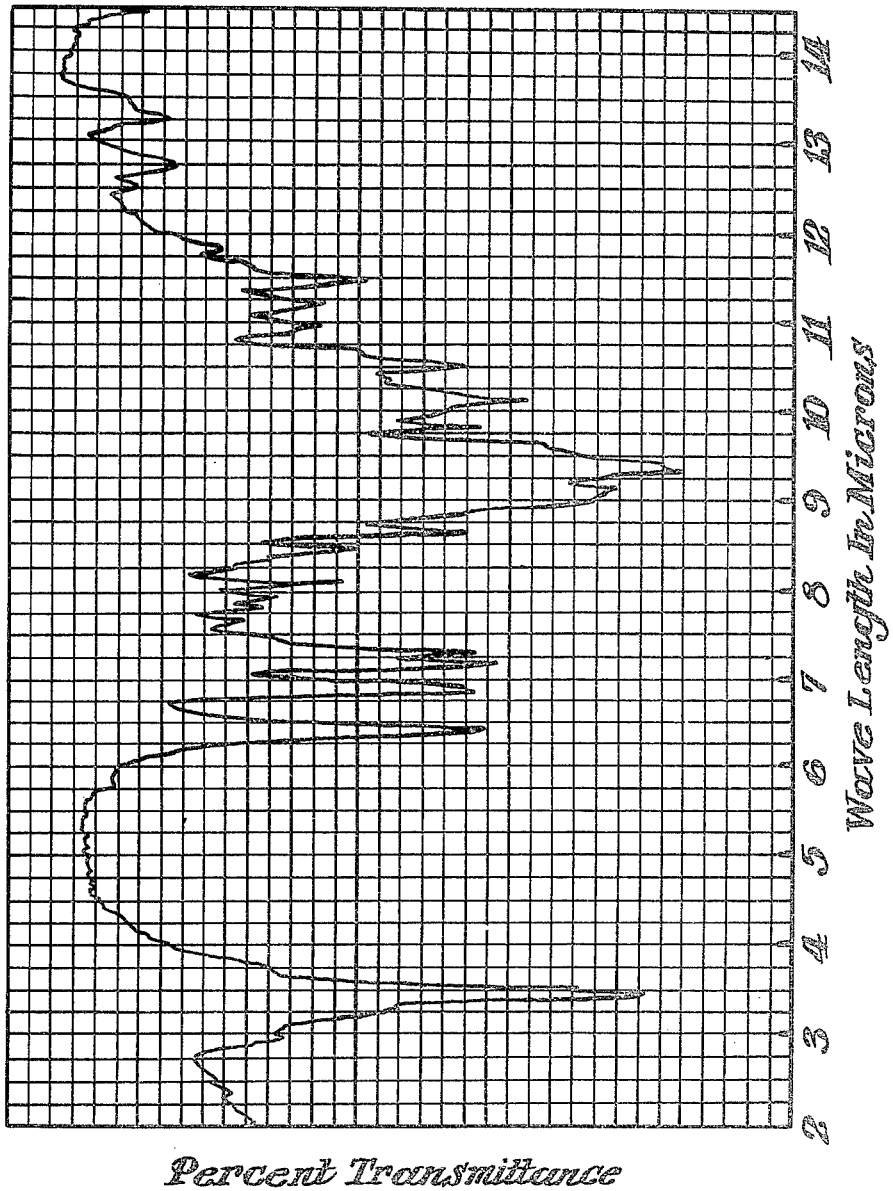

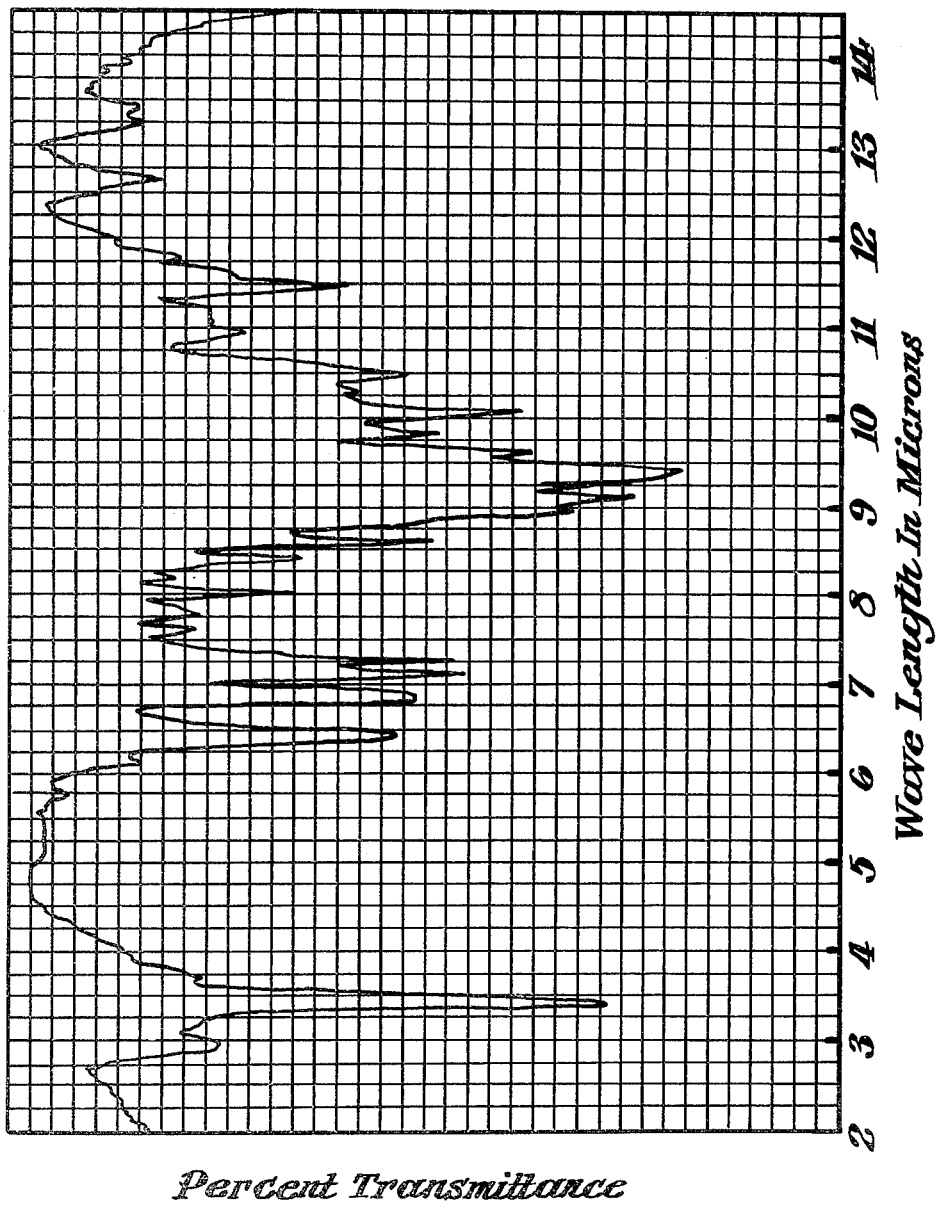

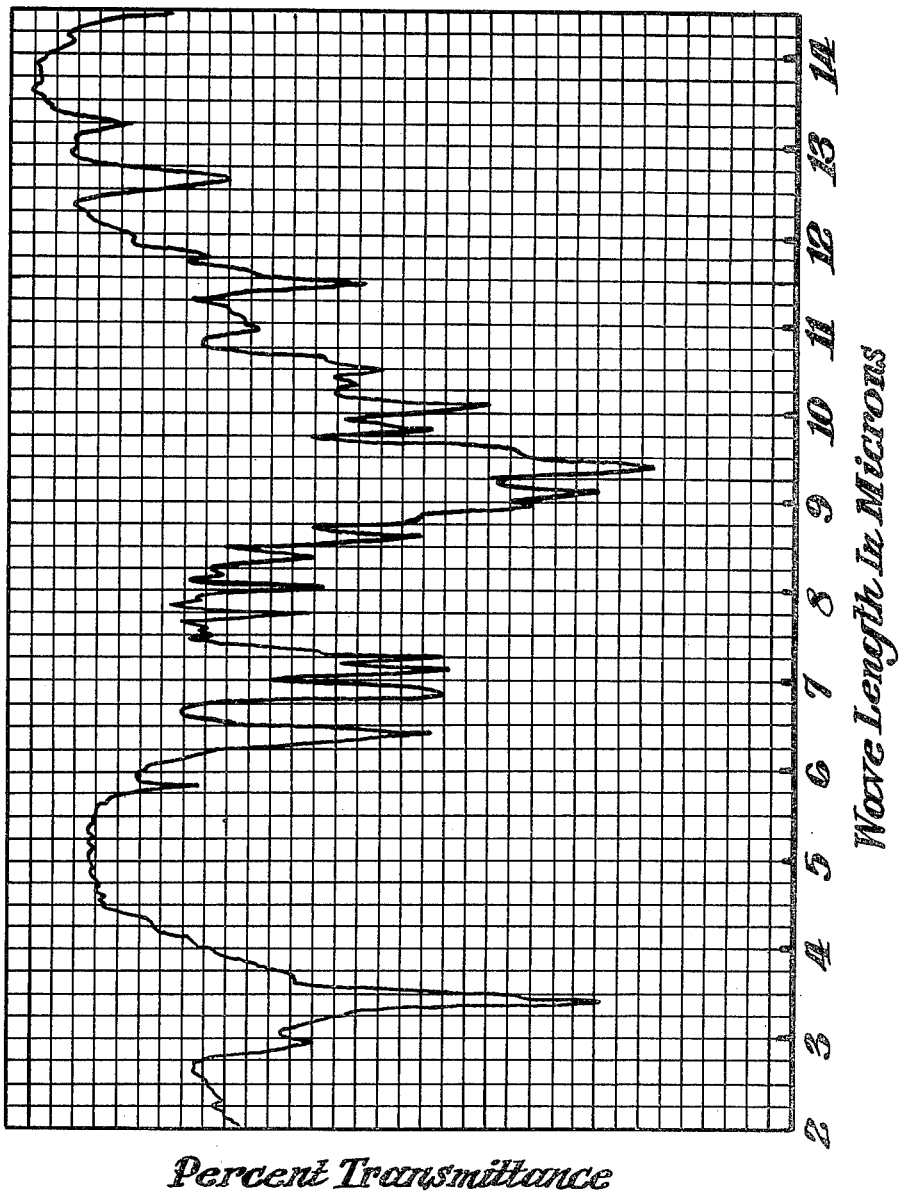

POLYCYCLIC ETHER ANTIBIOTICS PRODUCED BY NEW SPECIES OF ACTINOMYCETE

BACKGROUND OF THE INVENTION

This invention is concerned with new members of the acidic polycyclic ether group of antibiotics, a class of compounds characterized biologically by their effect on cation transport in mitochondria. This family of antibiotics includes monensin (J. Amer. Chem. Soc., 89:5737, 1967); nigericin (Biochem. Biophys. Pes. Comm. 33:29, 1968); grisorixin (J. Chem. Soc. Chem. Commun., 1421, 1970); dianemycin (J. Antibiotics, 22:161, 1969); salinomycin (J. Antibiotics, 27:814, 1974); X-537A (J. Chem. Soc. Chem. Commun., 967, 1972); X-206 (J. Chem. Soc. Chem. Commun., 927, 1971); and A204A (J. Amer. Chem. Soc., 95:3399 1973).

The polycyclic ether antibiotics listed above are active against Gram-positive bacteria, fungi and protozoa. These antibiotics exhibit potent anticoccidial activity.

The control of coccidiosis continues to be a serious problem to the poultry industry. There are six species of coccidia which produce easily discernible morbidity in susceptible chickens. *Eimeria tenella, E. necatrix, E. brunetti, E. acervulina, E. maxima* and *E. mivati* produce damage either directly through destruction of epithelial cells of the digestive tract or indirectly through production of toxins. Three other species of protozoa belonging to the same genus are considered to be relatively inocuous; however, *E. mitis, E. hagani* and *E. praecox are capable of reducing weight gain, lowering feed efficiency and adversely affecting egg production.*

The polycyclic ether antibiotics possess a high degree of effectiveness against all species of Eimeria. These antibiotics can, therefore, be regarded as "broad spectrum" coccidiostats.

SUMMARY OF THE INVENTION

This invention is concerned with new polycyclic ether antibiotics produced by a new species of Actinomadura macer Huang sp. Nov. ATCC 31286 under submerged aerobic conditions in aqueous nutrient media. Antibiotic Compounds 47,433 and 47,434 or mixtures of antibiotic Compounds 47,433 and 47,434 and their cationic salts are active against a variety of microorganisms, effective in controlling coccidiosis in poultry and act to improve feed utilization efficiency in ruminants.

DETAILED DESCRIPTION OF THE INVENTION

Figure 1:
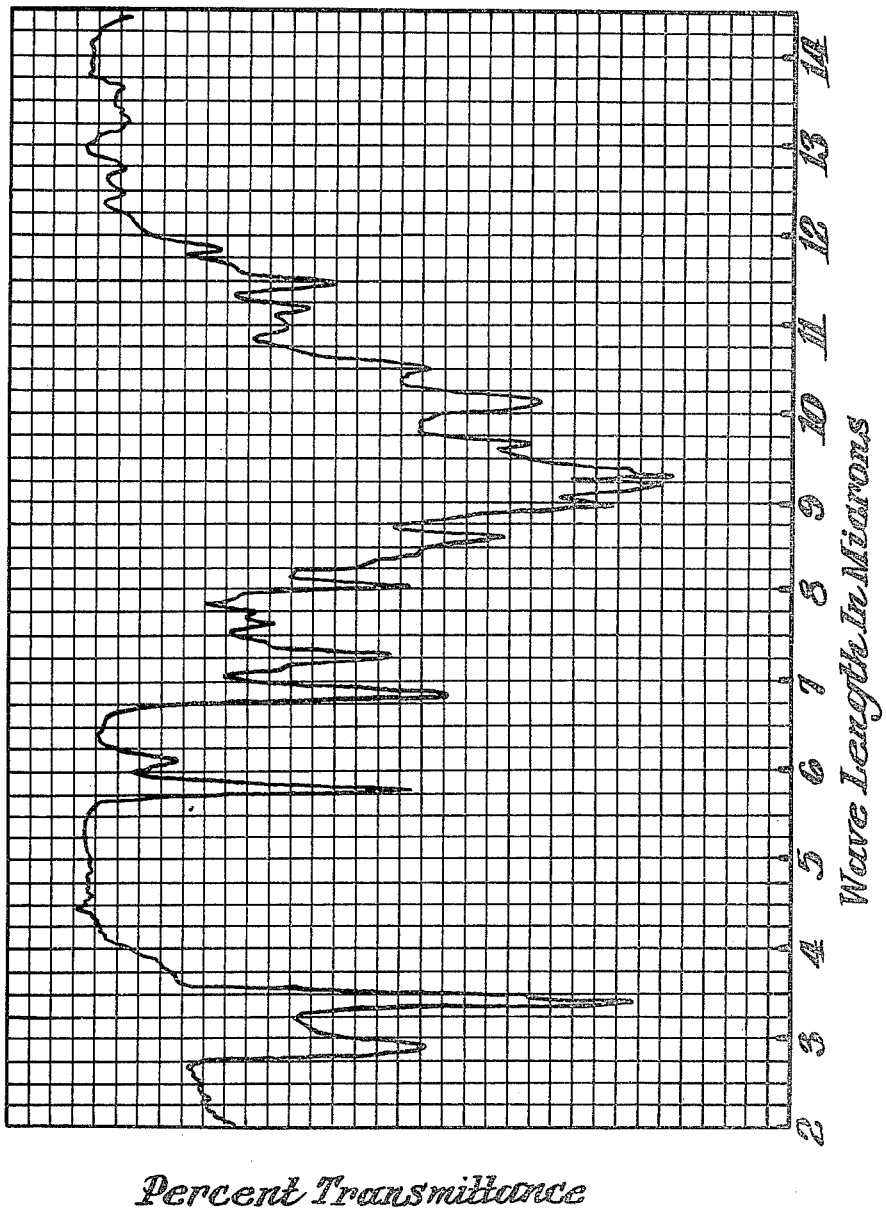

The antibiotic producing microorganism of the present invention, isolated from a soil sample in Japan, was found on examination to have the morphological features of an antinomycete such as narrow hyphae and sparse aerial mycelium. No spores were found on the media tested with the excpetion of tyrosine agar on which hyphal swellings were produced on substrate mycelium.

The culture was planted from an agar slant into liquid ATCC 172 medium (American Type Culture Catalogue, 10th edition p. 235, 1972) grown for 4 days at 28° C. on a rotary shaker and planted from the resultant growth to fresh liquid ATCC 172 medium. After 7 days of incubation at 28° C. on a shaker, it was centrifuged, washed twice with sterile distilled water and then planted on media commonly used for identification of members of the actinomycetes.

Inoculated media were incubated at 28° C. Readings of results were made at different times but most final results were recorded at the end of 14 days. The colors were described in common terminology but exact colors were determined by comparison with color chips from the Color Harmony Manual, fourth edition.

Identification media used for the characterization of the culture and references for their composition are as follows:

1. Tryptone-Yeast Extract Broth (ISP #1 medium, Difco).
2. Yeast Extract-Malt Extract Agar (ISP #2 medium, Difco).
3. Oatmeal Agar (ISP #3 medium, Difco).
4. Inorganic Salts-Starch Agar (ISP #4 medium, Difco).
5. Glycerol-Asparagine Agar (ISP #5 medium, Difco).
6. Peptone-Yeast Extract Iron Agar (ISP #6 medium, Difco).
7. Tyrosine Agar (ISP #7 medium, Difco).
8. Gelatin — R. E. Gordon and J. M. Mihm, Jr. Bact. 73: 15–27, 1957.
9. Starch — Ibid.
10. Potato Carrot Agar — M. P. Lechevalier, Jr. Lab. and Clinical Med. 71: 934–944, 1968 but use only 30 g potatoes, 2.5 g carrots and 20 g agar.
11. 2% Tap Water Agar.
12. Czapek-Sucrose Agar — S. A. Waksman, The Actinomycetes, Vol. 2, medium no. 1, p. 328.
13. Emerson's Agar — Ibid, medium no. 28, p. 331.
14. Nutrient Agar — Ibid, medium no. 14, p. 330.
15. Calcium Malate Agar — S. A. Waksman, Bact. Rev. 21: 1–29, 1957.
16. Peptone-Czapek Agar — J. N. Couch, Jr. Elisha Mitchell Soc. 79: 53–70, 1963.
17. Potato Dextrose Agar — Ibid.
18. Yeast Extract Soluble Agar — Ibid, Medium M-70a, p. 677.
19. Yeast Extract-Malt Extract Agar with coconut milk — ISP medium #2 plus 50 cc coconut milk per liter of medium.
20. Carbohydrates (ISP medium #9).

The culture (Pfizer F. D. 25934) was described as follows on the various media:

Yeast Extract-Malt Extract Agar — Growth good, greyish to greyish black (near grey series 2 dc to 2 dl), raised, wrinkled, with white to greyish aerial mycelium; reverse black; brownish soluble pigment.

Oatmeal Agar — Growth moderate, cream to faint pink (near grey series 3 ba), thin, smooth, with no to scant, short aerial mycelium; reverse like surface; no soluble pigment.

Inorganic Salts-Starch Agar — Growth very scant, colorless to pale greyish at end of streak (near grey series 2 fe), very thin, smooth; reverse colorless; no soluble pigment.

Glycerol-Asparagine Agar — Growth poor, cream (near grey series 1 ba), thin, smooth, with no to scant, short aerial mycelium; reverse like surface, no soluble pigment.

Tyrosine Agar — Growth poor, cream to pale yellowish (1 ca to 1 ea), thin, smooth, no aerial mycelium; reverse like surface; no soluble pigment.

Gelatin — Growth moderate, avellaneous (3 ec to 3 ge), slightly raised, wrinked but granular in some areas, no aerial mycelium; reverse like surface; no soluble pigment.

Starch — Growth moderate, avellaneous (4 ec to 4 ge), thin to slightly raised at the end of streak, smooth but slightly roughened at the end of streak, with scant white aerial mycelium in some areas; reverse like surface; no soluble pigment.

Potato Carrot Agar — Growth poor to moderate, pale greyish (near grey series 1 cb to 1 dc), thin, smooth; reverse like surface; no soluble pigment.

Tap Water Agar — Growth scant, colorless, thin, smooth, with no to scant, very short aerial mycelium; reverse like surface; no soluble pigment.

Czapek Sucrose Agar — Growth poor, pale cream (near grey series 2 ba), thin, smooth, no aerial mycelium; reverse colorless; no soluble pigment.

Emerson's Agar — Growth moderate to good, greyish black (near grey series 2 ih), raised, wrinkled; reverse like surface; no soluble pigment.

Nutrient Agar — Growth poor to moderate, cream (2 ca), smooth, with a few small, isolated black dots, no aerial mycelium; reverse like surface; no soluble pigment.

Calcium Malate Agar — Growth scant to poor, colorless to pale greyish (near grey series 2 dc to 2 fe), thin, smooth; reverse like surface; no soluble pigment.

Peptone Czapek Agar — Growth moderate, pinkish orange (5 ea to 5 ga), thin, smooth, no aerial mycelium; reverse like surface; no soluble pigment.

Potato Dextrose Agar — Growth moderate, greyish (near grey series 1 fe to 1 ih), thin, smooth to granular, with white to pale greyish aerial mycelium; reverse like surface; no soluble pigment.

Yeast Starch Agar — Growth moderate, pinkish orange (5 gc), thin, smooth to slightly granular, with scant white aerial mycellium in some areas; reverse like surface; pale yellowish soluble pigment.

Yeast Extract-Malt Extract Agar with Coconut Milk — Growth good, pale greyish (near grey series 2 dc to 2 ih), raised, granular to wrinkled, with white to pale greyish aerial mycelium; reverse greyish; brown soluble pigment.

Biochemical Properties — No melanin; no digestion of Ca malate; no soluble pigment on tyrosine; carbon utilization: on ISP #9 medium there were many doubtful results.

Morphological Properties — Hyphae narrow, branched, 0.4–0.6 μm in diam.; hyphal swellings produced on tyrosine agar, terminal or intercalary, scattered or contiguous, globose, oval, broadly elliptical to elongated, smooth, 1.5–3.5 μm in diam. or 2.8–5.5×1.1–2.8 μm.

Because of the hyphal swellings and absence of spores, the culture (Pfizer F.D. 25934) was classified as a species of Actinomadura macer Huang sp. Nov. ATCC 31286. It has been deposited at The American Type Culture Collection with the accession number ATCC 31286.

The permanency of the deposit of this culture at The American Type Culture Collection in Rockville, Md. and ready accessibility thereto by the public are afforded in the event the patent is granted. Access to the cultures is available during pendency of the application under Rule 14 and 35 USC 112. All restrictions on the availability to the public of the cultures deposited will be irrevocably removed upon granting of the patent.

Cultivation of Actinomadura macer Huang sp. Nov. ATCC 31286 culture preferably takes place in aqueous nutrient media at a temperature of 28°–36° C., and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks or the inoculum tanks may be seeded from the shake flasks. Growth in shaken flasks will generally have reached its maximum in 3 to 5 days whereas inoculum in submerged inoculum tanks will usually be at the most favorable period in 3 to 4 days. Substantial antibiotic activity is obtained in the final fermentor stage in approximately 3 to 5 days. The antibiotic levels range from 50 to 500 mg per liter.

The process of antibiotic production is conveniently followed during fermentation by biological assay of the broth employing a sensitive strain of *Staphylococcus aureus* or *Bacillus subtilis*. Standard plate assay technique is employed in which the zone of inhibition surrounding a filter paper disc saturated with the broth is used as a measure of antibiotic potency.

Thin-layer chromatography employing silica gel is a useful tool for analyzing the antibiotics produced in fermentation media and the composition of crude and purified materials extracted from the fermentation broths. The Analtech silica gel GF chromatograms are developed with ethyl acetate. The antibiotics, Compound 47,433 (major, least polar) and Compound 47,434 (minor, more polar) are visualized by spraying with 3% vanillin in ethanolic sulfuric acid (97:3 v/v). They show up as pinkish red spots on a white background on warming on a steam bath or a hot plate. Bio-overlay with agar seeded with a sensitive strain of *Staphylococcus aureus* or *Bacillus subtilis* is a further procedure for detection of these antibiotics.

The antibiotics may be separated and recovered by extracting the whole, unfiltered fermentation broth with an organic solvent such as chloroform, ethyl acetate, methylisobutyl ketone or butanol at a pH range of 4.0 to 10.0. A major portion of the antibiotic activity is contained in the mycelium and may be extracted therefrom by slurrying the separated mycelium with a water-soluble solvent such as methanol. The solvent is concentrated to a thin syrup.

A method of separation and recovery of antibiotics 47,433 and 47,434 is as follows: Separated wet mycelium from fermentation broth is extracted several times with methanol. The methanol is evaporated in vacuo to provide an aqueous extract which is extracted several times with chloroform. The chloroform extracts are combined and evaporated under vacuum to a viscous oil which is dissolved in heptane. Silica gel is added to the solution and the resultant slurry is evaporated to dryness on a rotary evaporator. The silica gel is placed on a large sintered glass funnel and washed with heptane, chloroform, ethyl acetate and acetone. The desired antibiotics are contained almost exclusively in the ethyl acetate fraction. This fraction is evaporated to dryness, re-dissolved in ethyl acetate and stirred with water. The pH is adjusted to 9.0 with 1.0 N sodium hydroxide. The ethyl acetate phase is separated, dried over anhydrous sodium sulfate and evaporated under vacuum. The residue is taken up in a small volume of methanol at which time crystallization occurs.

The crystalline material may be further purified by column chromatography employing silica gel developed with ethyl acetateheptane (30:70). Appropriate column cuts containing Compound 47,433 are combined and evaporated to dryness. The residue is dissolved in ethyl acetate and the pH adjusted to 5.0 while stirring with water. The ethyl acetate phase is separated and added to 5% disodium phosphate buffer and the pH adjusted to 9.0 with 1.0 N sodium hydroxide. The ethyl acetate phase is separated and dried over anhydrous sodium sulfate. The residue is taken up in acetone whereupon crystallization occurs.

Column cuts rich in the minor component Compound 47,434 are combined, chromatographed on silica gel and eluted with heptaneethyl acetate (1:1 v/v). Appropriate cuts are combined, washed with a pH 5.0 aqueous phase and then with disodium phosphate buffer at pH 9.0. The solvent phase is separated, dried over sodium sulfate and concentrated to dryness under vacuum. The residue is crystallized from acetone as the sodium salt of Compound 47,434.

Antibiotic Compound 47,433 and 47,434 exhibit inhibitory action against the growth of a number of Gram-positive microorganisms. These compounds and their cationic salts exhibit excellent activity against coccidiosis infections in poultry. When incorporated into the diet of chickens at levels of 2.5 to 100 ppm, these compounds are effective in controlling infections due to *Eimeria tenella, E. acervulina, E. maxima, E. brunetti* and *E. necatrix*.

Efficacy data for Compound 47,433 and its cationic salts against coccidiosis infections in chickens was obtained as follows: Groups of 3–5 ten-day old SPF white leghorn cockerel chicks were fed a mash diet containing antibiotic Compound 47,433 or its sodium and/or potassium salt uniformly dispersed therein. After being on this ration for 24 hours, each chick was inoculated per os with oocysts of the particular species of Eimeria being tested. Other groups of 3–5 ten day-old chicks were fed a similar mash diet free from antibiotic Compound 47,433 or its salts. They were also infected after 24 hours and served as infected controls. Still other groups of chicks were fed the mash diet free of antibiotic Compound 47,433 and were not infected with coccidiosis. These served as normal controls. The results of treatment were evaluated after five days in the case of *E. acervulina* and six days for all other challenges.

| Species Infection | Dose (ppm) | Average Degree[1] of Infection | Ratio[1] | Weight Gain (%) |
|---|---|---|---|---|
| *Eimeria tenella* | 60 | 0.0 | 0.0 | 0 |
| | 30 | 0.0 | 0.0 | 16 |
| | 15 | 0.0 | 0.0 | 36 |
| | 7.5 | 1.7 | 0.47 | 75 |
| *Eimeria Acervulina* | 60 | 0.5 | 0.31 | 29 |
| | 30 | 0.4 | 0.25 | 39 |
| | 15 | 0.6 | 0.38 | 51 |
| | 7.5 | 0.6 | 0.38 | 49 |
| *Eimeria necatrix* | 60 | 0.0 | 0.0 | 0 |
| | 30 | 0.0 | 0.0 | 36 |
| | 15 | 0.2 | 0.06 | 94 |
| | 7.5 | 0.8 | 0.27 | 83 |
| *Eimeria maxima* | 60 | 0.6 | 0.43 | 0 |
| | 30 | 0.4 | 0.29 | 23 |
| | 15 | 0.6 | 0.43 | 53 |
| | 7.5 | 0.4 | 0.29 | 106 |
| *Eimeria brunetti* | 60 | 0.0 | 0.0 | 8 |
| | 30 | 0.2 | 0.13 | 45 |
| | 15 | 0.2 | 0.13 | 94 |
| | 7.5 | 0.6 | 0.38 | 100 |

[1]The criteria used to measure anticoccidial activity consisted of lesion scores of 0 to 4 for *E. tenella* after J. E. Lynch (1961, A new method for the primary evaluation of anticoccidial activity. Am. J. Vet. Res. 22:324–326); and 0 to 3 for the other species based on a modification of the scoring system devised by J. Johnson and W. H. Reid (1970, Anticoccidial drugs. Lesion scoring techniques in battery and floor pen experiments in chicks. Exp. parasit. 28:30–36). A constant ratio was established by dividing the lesion score of each treated group by the lesion scored of the infected control.

Substantially the same results may be obtained with antibiotic Compound 47,434 or mixtures of antibiotic Compound 47,433 and antibiotic Compound 47,434.

The value of animal feeds generally has been determined directly by feeding the animal. G.B. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taking place are studied critically and progressively during the consumption of the feed by the microorganisms. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml added to a 50 ml conical flask containing 400 mg. of standard substrate (68% corn starch + 17% cellulose + 15% extracted soybean meal), 10 ml of a pH 6.8 buffer and the test compound. The flasks are gassed with oxygen free nitrogen for about two minutes, and incubated in a shaking water bath at 39° C. for about 16 hours. All tests are conducted in triplicate.

After incubation 5 ml of the sample are mixed with 1 ml of 25% metaphosphoric acid. After 10 minutes 0.25 ml of formic acid is added and the mixture centrifuged at 1.500 r.p.m. for 10 minutes. Samples are then analyzed by gas-liquid chromatography by the method of D. W. Kellog in J. Dairy Science 52, 1690 (1969). Peak heights for acetic, propionic and butyric acids are determined for samples from untreated and treated incubation flasks.

When tested by this in vitro procedure, the sodium salt of Compound 47,433 (20 ppm) gave rise to a 50% increase in the production of propionic acid over that produced in the control solution without added Compound 47,433. Similar results may be obtained with the free acid or other pharmaceutically-acceptable salts, antibiotic Compound 47,434 or its pharmaceutically-acceptable salts or mixtures of Compounds 47,433 and 47,434.

Substantially the same results may be obtained with the free acid, potassium salt or mixtures of the free acid, potassium salt and sodium salt of the antibiotic Compound 47,433. Similar results may be obtained with antibiotic Compound 47,434 or mixtures of pure Compounds 47,433 and 47,434 or the cationic salts thereof.

Based on these data, it can be projected that improvement of feed utilization by ruminants such as cattle and sheep and monogastric animals such as horses, pigs and rabbits will be comparable with that obtained by commercially available Monensin, a polycyclic ether antibiotic. Antibiotic Compounds 47,433 and 47,434 and mixtures of antibiotic Compounds 47,433 and 47,434 may be incorporated in feed compositions as the free acid, sodium salt, potassium salt or mixtures thereof. Crude antibiotic mixtures of Compounds 47,433 and 47,434 or dried fermentation broth containing the two antibiotics may be incorporated in feed compositions at the desired potency concentrations.

EXAMPLE I

A sterile aqueous medium having the following composition was prepared:

| Ingredient | Grams/liter |
| --- | --- |
| Glucose | 10 |
| Starch | 20 |
| Yeast extract | 5 |
| Enzymatic digest of casein | 5 |
| Dipotassium hydrogen phosphate | 0.5 |
| Meat real | 5 |
| Cobalt chloride | 0.002 |
| Calcium carbonate | 4 |
| pH 7.1–7.2 | |

Cells from a slant of Actinomadura macer Huang sp. nov. ATCC 31286 were transferred to a series of 300 ml flasks each containing 50 ml of this sterile medium and shaken on a rotary shaker at 28°–30° C. for 3–4 days. An aliquot of the grown culture, sufficient to provide a 5% v/v inoculum, was transferred to four-liter fermentors each containing two liters of the following sterile medium:

| Ingredient | Grams/liter |
| --- | --- |
| Glucose | 20 |
| Soy flour | 30 |
| Ferric sulfate | 0.3 |
| Manganese chloride | 0.3 |
| Cobalt chloride | 0.002 |
| pH 6.9–7.1 | |

The fermentation was conducted at 28°–36° C. with stirring at 1700 revolutions per minute and aeration at 1.5 to 2 volumes of air per volume of broth per minute until substantial activity was obtained (48–120 hours). The whole broth, without pH adjustment, was twice extracted with ⅓ to ½ volume of methylisobutyl ketone. The separated solvent extracts were combined and concentrated under vacuum to a thin syryp.

EXAMPLE 2

The inoculum medium of Example 1 was distributed in 700 ml amounts in 4 to 8 shake flasks and inoculated with cells of Actinomycete sp. ATCC 31286. After incubation at 28° C. on a rotary shaker for 3 to 8 days, a 3 to 5% v/v inoculum was introduced into a 50 gallon fermentor container twenty five gallons of the following sterile medium:

| Ingredient | Grams/liter |
| --- | --- |
| Glucose | 1 |
| Soy fluor | 10 |
| Corn starch | 10 |
| Grain solubles | 5 |
| Ferric sulfate | 0.2 |
| Manganese chloride | 0.2 |
| Cobalt chloride | 0.002 |
| Sodium chloride | 5 |
| Methyl oleate | 2 |
| Calcium carbonate | 1 |
| Soybean oil | 2 |
| pH 6.9–7.1 | |

The fermentation was conducted for a period of 5 days at 30° C. with an aeration rate of one volume of air per volume of medium per minute.

The separated mycelium from 25 gallons of broth was extracted three times with 5 gallons (each time) of methanol. The combined methanolic extracts were evaporated under vacuum to provide an aqueous extract of about 3 gallons which was extracted 4 times with one gallon (each time) of chloroform. The chloroform extracts were combined and evaporated under vacuum to yield 51 grams of a viscous yellow oil. The oil was dissolved in 500 ml of heptane. Column grade silica gel 60 (E. Merck, Darmstadt, Germany), about 500 grams, was added to the solution and the resultant slurry was evaporated to dryness on a rotary evaporator.

The silica gel was then placed on a large sintered glass funnel and washed successively with two liters each of heptane, chloroform, ethyl acetate and acetone. The desired antibiotics were shown by thin-layer chromatography to be contained almost exclusively in the ethyl acetate fraction. This fraction was evaporated to dryness (24 grams) and the other fractions were discarded.

The material was dissolved in 125 ml of ethyl acetate and stirred with 125 ml of water. The pH was raised to 9.0 with 1.0 N sodium hydroxide. The ethyl acetate phase was dried over anhydrous sodium sulfate and evaporated in vacuo. The residue was taken up in a small volume of methanol at which time crystallization occurred. The crystals were removed by filtration and washed with methanol (5.1 grams).

The crude crystalline material was further purified by column chromatography on a 2.54×100 cm column packed with silica gel 60 in heptane. A portion of the crude crystalline material (2.5 grams) was applied to the column in solution in ethyl acetate-heptane (30:70) and the column developed with the same solvent system at a rate of 10 ml/minute with column cuts taken every two minutes. The column cuts were monitored by thin-layer chromatography. Following completion of the chromatography, the column was washed with heptane, and the remaining 2.6 grams of crude crystalline material processed in the same manner.

Appropriate cuts containing the major antibiotic component Compound 47,433 were combined and evaporated to dryness. The residue was dissolved in 100 ml of ethyl acetate and the pH adjusted to 5.0 with 85% phosphoric acid while stirring with 100 ml of water. The ethyl acetate phase was added to 100 ml of 5% disodium phosphate buffer and the pH adjusted to 9.0 with 1 N sodium hydroxide. The ethyl acetate phase was dried with anhydrous sodium sulfate and evaporated to dryness. The residue was taken up in acetone whereupon crystallization occurred. Crystals were collected by filtration and dried under high vacuum at room temperature to yield 2.7 grams of Compound 47,433 as the sodium salt.

Those column cuts rich in minor component Compound 47,434 were combined and chromatographed on silica gel 60 eluting with heptane: ethyl acetate (1:1 v/v). Appropriate cuts were combined, washed with a pH 5.0 aqueous phase with a subsequent wash with a pH 9.0 (disodium phosphate buffer adjusted to pH 9.0 with 1.0 N sodium hydroxide) aqueous phase. The solvent phase was dried over sodium sulfate and concentrated in vacuo to dryness. The residue was crystallized from acetone as the sodium salt (170 mg) of Compound 47,434.

Compound 47,433 (sodium salt)

The sodium salt of Compound 47,433 is soluble in chloroform, ethyl acetate and methylisobutyl ketone; it is insoluble in water. The sodium salt, m.p. 226°–232° C., is characterized by an average composition by weight of 62.75% carbon and 9.21% hydrogen; an optical rotation of $[\alpha]_D = -0.2°$ (c=1.0, methanol); no ultraviolet light absorption spectrum; and when pelleted in KBr, distinguishable bands in the infrared region as shown in FIG. 2 at the following wavelengths in microns: 3.40, 6.40, 6.85, 7.12, 7.25, 8.02, 8.38, 8.60, 9.40, 10.05, 10.49, 11.45, 12.65 and 13.25.

Compound 47,433 (free acid)

The free acid was derived by washing an ethyl acetate solution of the sodium salt of Compound 47,433 with a pH 5.0 aqueous phase (water adjusted to pH 5.0 with 85% phosphoric acid). The solvent layer was concentrated in vacuo and crystallized from heptane as the free acid.

The free acid, m.p. 80°–99° C., is soluble in methanol, acetone, chloroform, methylisobutyl ketone and ethyl acetate; it is insoluble in water.

The free acid is characterized by an average composition by weight of 64.92% carbon, 9.73% hydrogen and 25.35% oxygen (by difference); an optical rotation of $[\alpha]_D = +16°$ (c=1.0, methanol); no ultraviolet light absorption spectrum; and when pelleted in KBr, distinguishable bands in the infrared region as shown in FIG. 1 at the following wavelengths in microns: 2.87, 3.42, 5.77, 6.85, 7.30, 8.05, 8.60, 9.20, 10.15, 10.53 and 11.45.

Compound 47,433 (potassium salt)

The potassium salt of Compound 47,433 was obtained by washing an ethyl acetate solution of the free acid with aqueous dipotassium hydrogen phosphate adjusted to pH 9.0 with 1.0 N potassium hydroxide. It was crystallized from heptane.

The potassium salt, m.p. 202°–205° C. is soluble in chloroform, ethyl acetate and methylisobutyl ketone; it is insoluble in water. The compound is characterized by an average composition by weight of 62.57% carbon and 9.01% hydrogen; no ultraviolet light absorption spectrum; an optical rotation of $[\alpha]_D = -3.2°$ (c=1.0, methanol); and when pelleted in KBr, distinguishable bands in the infrared region as shown in FIG. 3 at the following wavelengths in microns: 3.45, 6.40, 6.85, 7.16, 7.30, 8.05, 8.45, 8.65, 9.40, 10.13, 10.52 and 11.48.

Compound 47,433 (silver salt)

The silver salt of Compound 47,433 was prepared by the addition of silver nitrate in aqueous methanol to an aqueous methanolic solution of the sodium salt. Removal of the methanol under vacuum led to the separation of the silver salt. The salt is soluble in chloroform, ethyl acetate and methylisobutyl ketone; it is insoluble in water.

The silver salt of Compound 47,433, m.p. 180°–182° C., is characterized by an average composition by weight of 57.85% carbon and 8.31% hydrogen; no ultraviolet light absorption spectrum; an optical rotation of $[\alpha]_D = +3.6°$ (c=1.0, methanol); and when pelleted in KBr, distinguishable bands in the infrared region as shown in FIG. 4 at the following wavelengths in microns: 3.40, 6.45, 6.85, 7.10, 7.25, 8.04, 8.60, 9.12, 9.40, 10.08, 10.49, 11.47 and 12.65.

Compound 47,434 (sodium salt)

The sodium salt of Compound 47,434 is soluble in chloroform, ethyl acetate and methylisobutyl ketone; it is insoluble in water. The crystalline compound, m.p. 230°–238° C., is characterized by an average composition by weight of 62.31% carbon and 9.12% hydrogen; an optical rotation of $[\alpha] = -1.3°$ (c=1.0, methanol); no ultraviolet light absorption spectrum; and when pelleted in KBr, distinguishable bands in the infrared region as shown in FIG. 5 at the following wavelengths in microns: 3.40, 6.40, 6.85, 7.14, 7.27, 7.75, 8.05, 8.40, 8.62, 9.10, 9.40, 10.17, 10.50, 11.49, 12.65 and 13.25.

We claim:

1. The antibiotic Compound 47,433, or a pharmaceutically acceptable cationic salt thereof, said antibiotic when in the form as the crystalline free acid is soluble in methanol, acetone, chloroform, methylisobutyl ketone, ethyl acetate and insoluble in water; has a melting point of 89°–99° C.; an optical rotation of $[\alpha]_D = +16°$ at a concentration of 1% in methanol; an average composition by weight of 64.92% carbon, 9.73% hydrogen and 25.35% oxygen (by difference); and when pelleted in KBr, exhibits characteristic absorption in the infrared region at the following wavelengths in microns: 2.87, 3.42, 5.77, 6.85, 7.30, 8.05, 8.60, 9.20, 10.15, 10.53 and 11.45.

2. The antibiotic Compound 47,433 of claim 1 when in the form as the crystalline sodium salt.

3. The antibiotic Compound 47,433 of claim 1 when in the form as the crystalline potassium salt.

4. The antibiotic Compound 47,433 of claim 1 when in the form as the crystalline silver salt.

5. The antibiotic Compound 47,434, or a pharmaceutically acceptable cationic salt thereof, said antibiotic when in the form as the crystalline sodium salt is soluble in chloroform, ethyl acetate, methylisobutyl ketone and insoluble in water; has a melting point of 230°–238° C.; an optical rotation of $[\alpha]_D = -1.3°$ at a concentration of 1% in methanol; an average composition by weight of 62.31% carbon and 9.12% hydrogen; and when pelleted in KBr, exhibits characteristic absorption in the infrared region at the following wavelengths in microns: 3.40, 6.40, 6.85, 7.14, 7.27, 7.75, 8.05, 8.40, 8.62, 9.10, 9.40, 10.07, 10.50, 11.49, 12.65 and 13.25.

6. A process for producing an antibiotic complex which comprises cultivating the microorganism Actinomadura macer Huang sp. nov. ATCC 31286 in aqueous culture media containing an assimilable source of carbon, nitrogen and inorganic salts until substantial antibiotic activity is obtained.

7. The antibiotic complex produced by the process of claim 6.

8. A process according to claim 6 wherein said antibiotic complex is separated from the fermentation medium.

9. A process according to claim 6 wherein the fermentation medium is taken to dryness.

* * * * *